(12) United States Patent
Muto et al.

(10) Patent No.: US 7,915,418 B2
(45) Date of Patent: Mar. 29, 2011

(54) INTERMEDIATES AND PROCESS FOR THE PRODUCTION OF OPTICALLY ACTIVE QUINOLONECARBOXYLIC ACID DERIVATIVES

(75) Inventors: Makoto Muto, Tokyo (JP); Manabu Miura, Tokyo (JP); Yutaka Kitagawa, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 1107 days.

(21) Appl. No.: 10/559,499

(22) PCT Filed: Jun. 4, 2004

(86) PCT No.: PCT/JP2004/007813
§ 371 (c)(1),
(2), (4) Date: Dec. 5, 2005

(87) PCT Pub. No.: WO2004/108680
PCT Pub. Date: Dec. 16, 2004

(65) Prior Publication Data
US 2006/0135775 A1    Jun. 22, 2006

(30) Foreign Application Priority Data
Jun. 6, 2003  (JP) ................. 2003-162558

(51) Int. Cl.
C07D 215/38    (2006.01)
(52) U.S. Cl. .......................... 546/156; 546/153
(58) Field of Classification Search ............ 546/156, 546/153
See application file for complete search history.

(56) References Cited

U.S. PATENT DOCUMENTS

| | | | | |
|---|---|---|---|---|
| 5,545,642 A | * | 8/1996 | Petersen et al. | 514/312 |
| 5,849,757 A | * | 12/1998 | Takemura et al. | 514/312 |
| 6,900,225 B2 | * | 5/2005 | Takemura et al. | 514/312 |
| 7,482,454 B2 | | 1/2009 | Ledoussal et al. | |
| 2004/0063754 A1 | | 4/2004 | Takahashi et al. | |

FOREIGN PATENT DOCUMENTS

| | | |
|---|---|---|
| EP | 1 182 202 A1 | 2/2002 |
| EP | 1 298 131 A1 | 4/2003 |
| EP | 1 336 611 A1 | 8/2003 |
| JP | 63-316757 | 12/1988 |
| JP | 2001-516756 | 10/2001 |
| WO | WO 99/14214 | 3/1999 |
| WO | 01-72738 | 10/2001 |
| WO | 02-40478 | 5/2002 |
| WO | 2004-013103 | 2/2004 |

OTHER PUBLICATIONS

U.S. Appl. No. 10/560,823, filed Dec. 15, 2005, Muto, et al.

* cited by examiner

Primary Examiner — D. Margaret Seaman
(74) Attorney, Agent, or Firm — Oblon, Spivak, McClelland, Maier & Neustadt, L.L.P.

(57) ABSTRACT

Provision of a commercially advantageous method for producing an intermediate which is important for producing the antibacterial and which has a mother nucleus common to the antibacterial, and intermediates produced by such method.
A method for producing a compound represented by formula (VI):

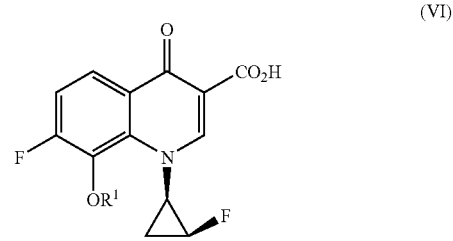

which comprises the steps of treating a compound represented by formula (IV):

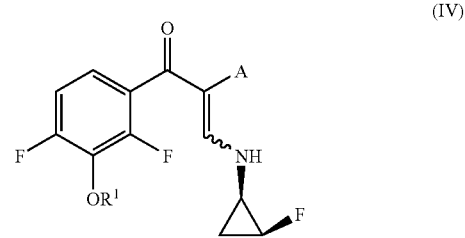

with a base in the presence of a base to produce a compound represented by formula (V):

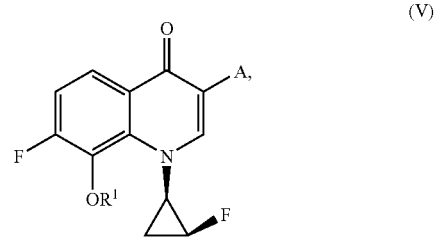

and hydrolyzing this compound;

a compound represented by formula (II):
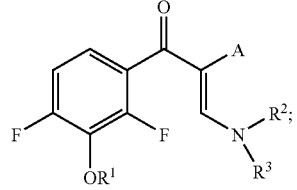
(II)
a compound represented by formula (Ia):
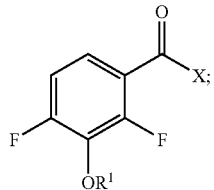
(Ia)
a compound represented by formula (V):
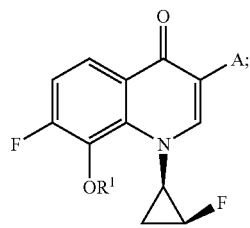
(V)
and a compound represented by formula (VI).
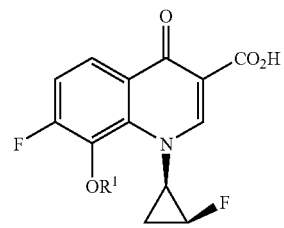
(VI)
16 Claims, No Drawings

INTERMEDIATES AND PROCESS FOR THE PRODUCTION OF OPTICALLY ACTIVE QUINOLONECARBOXYLIC ACID DERIVATIVES

TECHNICAL FIELD

This invention relates to a method for producing a 6-H quinolonecarboxylic acid derivative ("6-H" means that the compound is substituted with hydrogen at 6-position) which is an intermediate in synthesizing quinolonecarboxylic acid antibacterials, as well as to novel intermediates in producing such quinolonecarboxylic acid derivative. The quinolonecarboxylic acid antibacterials are highly promising as medicaments, agricultural chemicals and veterinary drugs.

BACKGROUND ART

Quinolonecarboxylic acid derivatives are widely used in medicine as synthetic antibacterials. However, emergence of resistant bacteria represented by MRSA has become a major obstacle in such treatments. A quinolonecarboxylic acid derivative represented by the following formula (A):

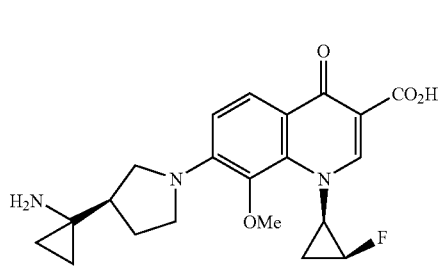

(A)

is a compound capable of overcoming the problems associated with various resistant bacteria since this not only exhibits excellent effects on MRSA but also has an antibacterial activity against resistant Gram-positive bacteria. A known process for producing an intermediate having the mother nucleus of quinolonecarboxylic acid is shown by the following reaction scheme (see, for example, Patent Document 1).

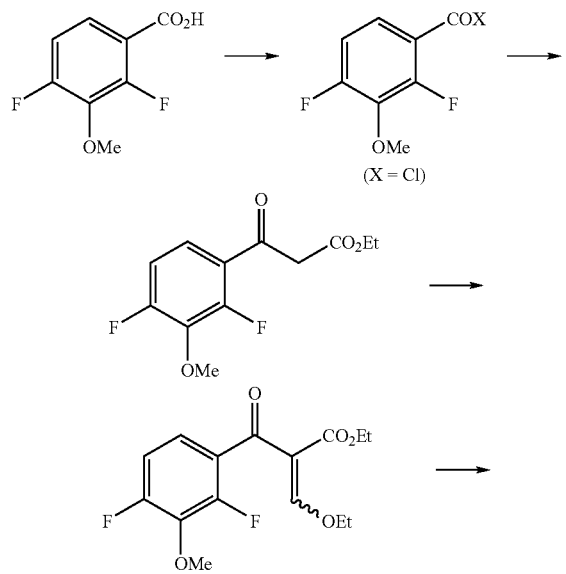

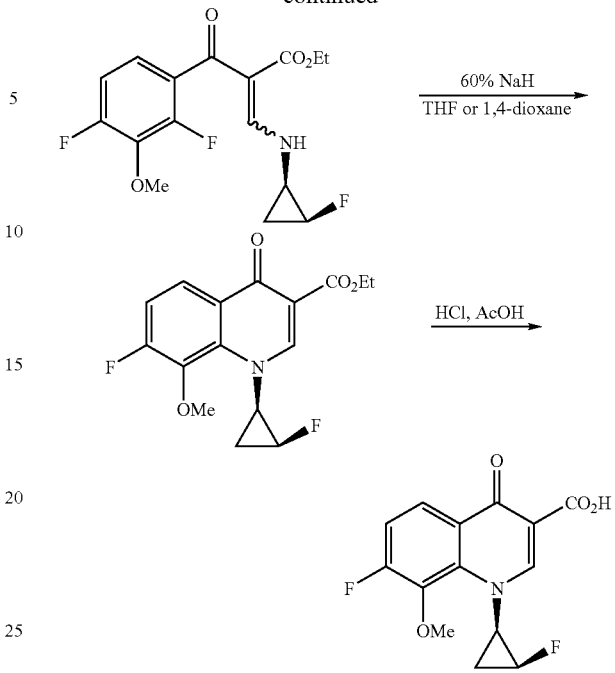

Patent Document 1: WO 02/040478 gazette

DISCLOSURE OF THE INVENTION

Problems to be Solved by the Invention

The production methods currently known in the art, however, require a large number of steps, and further, these include the step of using an organolithium reagent at an extremely low temperature (−50° C.), and such step places a serious burden on the production process and hampers commercial use of such method on a large scale.

Accordingly, the objects of the present invention are to provide a commercially advantageous method for producing an intermediate which is important in producing an antibacterial and which has a mother nucleus common to the antibacterial, as well as to provide intermediates produced by such method.

Means to Solve the Problems

The present inventors have made an extensive investigation, and have found that a 7-fluoro-1-[(1R,2S)-2-fluorocyclopropylamine]-1,4-dihydro-8-alkoxy-4-oxoquinoline-3-carboxylic acid can be produced in a commercially advantageous manner in 5 steps, for example, as shown by the reaction scheme described below, by converting a 2,4-difluoro-3-alkoxybenzoic acid into an acid chloride or a mixed acid anhydride, condensing it with an ethyl N,N-dialkylaminoacrylate to produce a 3-dialkylamino-2-(2,4-difluoro-3-alkoxybenzoyl)acrylic acid derivative, and using the derivative as a key intermediate in producing the 7-fluoro-1-[(1R, 2S)-2-fluorocyclopropylamine]-1,4-dihydro-8-alkoxy-4-oxoquinoline-3-carboxylic acid to complete the present invention.

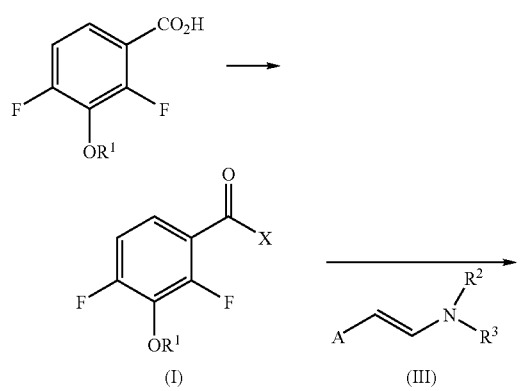

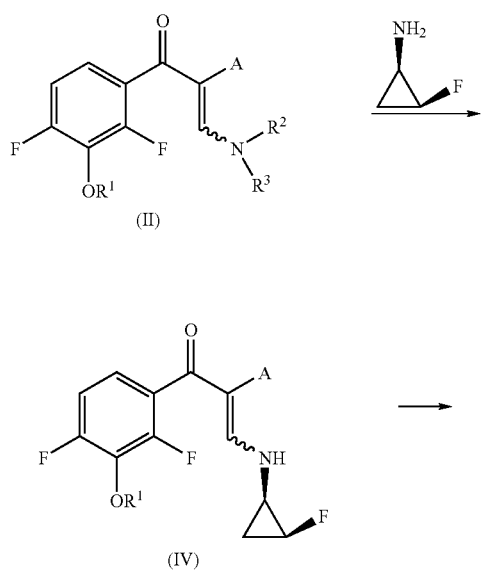

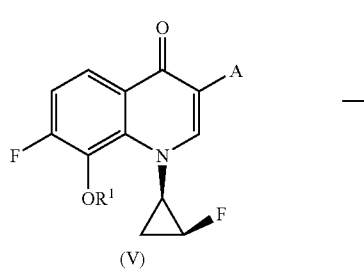

In this reaction scheme, X represents a halogen atom or an acyloxy group, $R^1$ represents a lower alkyl group, $R^2$ and $R^3$ represent the same or different lower alkyl groups, and A represents nitrile group or an alkoxycarbonyl group.

Accordingly, this invention provides a method for producing a compound represented by the following formula (VI):

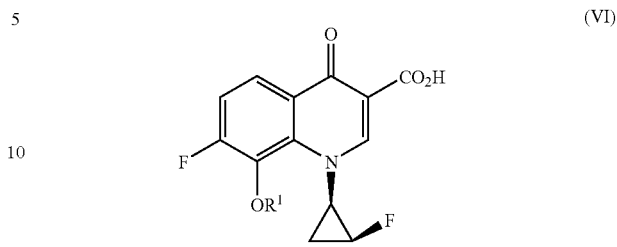

wherein $R^1$ represents a lower alkyl group which comprises the steps of treating a compound represented by formula (IV):

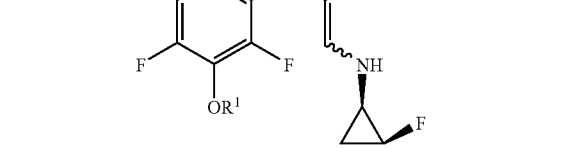

wherein $R^1$ is as defined above and A represents nitrile group or an alkoxycarbonyl group with a base to produce a compound represented by formula (V):

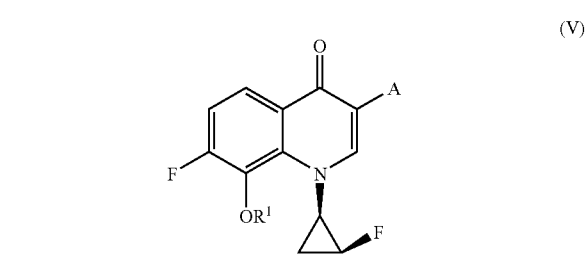

wherein $R^1$ is as defined above, and hydrolyzing this compound.

The compound represented by formula (IV) can be produced by reacting a compound represented by formula (II):

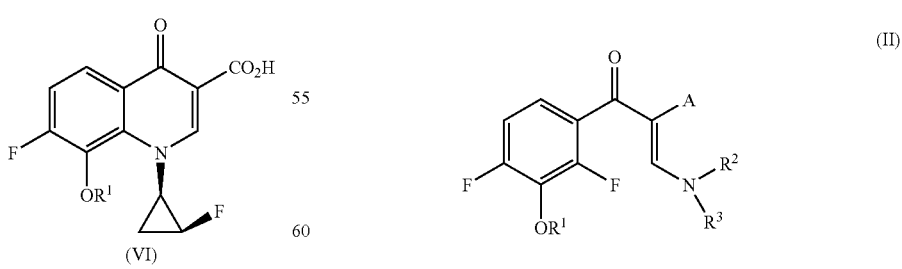

wherein $R^2$ and $R^3$ represent the same or different lower alkyl groups, and $R^1$ and A are as defined above with (1R,2S)-2-fluorocyclopropylamine.

The compound represented by formula (II) can be produced by reacting a compound represented by formula (I):

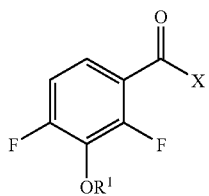

wherein X represents a halogen atom or an acyloxy group and $R^1$ is as defined above with a compound represented by formula (III)

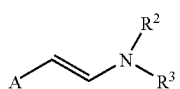

wherein A, $R^2$, and $R^3$ are as defined above.

The compound represented by formula (I) can be produced by reacting a compound represented by the following formula:

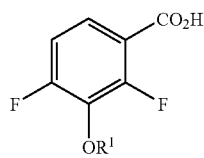

wherein $R^1$ is as defined above with a halogenating agent or an acid anhydride.

This invention also provides a compound represented by formula (II):

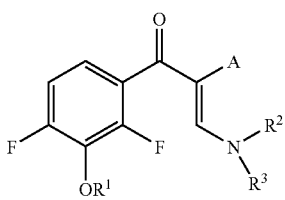

wherein $R^1$ represents a lower alkyl group, A represents nitrile group or an alkoxycarbonyl group, and $R^2$ and $R^3$ represent the same or different lower alkyl groups. This compound is an intermediate useful for synthesizing the compound represented by formula (VI) which is an intermediate in producing 6-H quinolonecarboxylic acid derivatives having a strong antibacterial activity and which has a mother nucleus common to the 6-H quinolonecarboxylic acid derivatives.

This invention also provides a compound represented by formula (Ia):

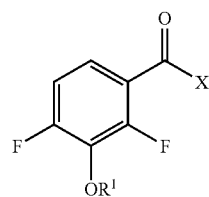

wherein $R^1$ represents a lower alkyl group and X represents an acyloxy group. This compound is an intermediate useful for synthesizing the compound represented by the formula (VI) which is an intermediate in producing 6-H quinolonecarboxylic acid derivatives having a strong antibacterial activity and which has a mother nucleus common to the 6-H quinolonecarboxylic acid derivatives.

This invention also provides a compound represented by formula (V):

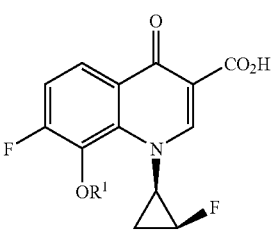

wherein $R^1$ represents a lower alkyl group and A represents nitrile group or an alkoxycarbonyl group. This compound is an intermediate useful for synthesizing the compound represented by formula (VI) which is an intermediate in producing 6-H quinolonecarboxylic acid derivatives having a strong antibacterial activity and which has a mother nucleus common to the 6-H quinolonecarboxylic acid derivatives.

This invention also provides a compound represented by formula (VI):

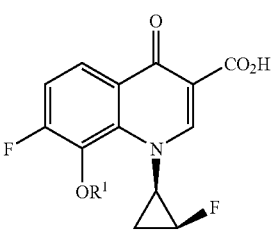

wherein $R^1$ represents a lower alkyl group. This compound is an intermediate useful for synthesizing the compound represented by formula (VI) which is an intermediate in producing 6-H quinolonecarboxylic acid derivatives having a strong antibacterial activity and which has a mother nucleus common to the 6-H quinolonecarboxylic acid derivatives.

Effects of the Invention

The method according to the present invention is commercially quite advantageous since it reduces the number of production steps and does not involve low reaction temperature nor use of reagents which are difficult to handle.

EMBODIMENTS TO CARRY OUT THE INVENTION $R^1$ in formulae (I), (II) and (IV) to (VI) is preferably a straight or branched lower alkyl group containing 1 to 3 carbon atoms such as methyl, ethyl, n-propyl, or isopropyl. $R^1$ is most preferably methyl group.

$R^2$ and $R^3$ in formulae (II) and (III) is preferably a straight or branched lower alkyl group containing 1 to 4 carbon atoms such as methyl, ethyl, n-propyl, isopropyl, n-butyl, isobutyl, or sec-butyl. $R^2$ and $R^3$ are more preferably methyl group or ethyl group, and most preferably methyl group.

A in formulae (II) to (V) is preferably nitrile group or an alkoxycarbonyl group containing 2 to 5 carbon atoms such as methoxycarbonyl, ethoxycarbonyl, n-propoxycarbonyl, isopropoxycarbonyl, n-butoxycarbonyl, or isobutoxycarbony. A is most preferably methoxycarbonyl or ethoxycarbonyl.

X in formula (I) is preferably a halogen atom such as chlorine or bromine, an alkanoyloxy group containing 2 to 6 carbon atoms such as acetoxy group or propionyloxy group, a halogenated alkanoyloxy group containing 2 to 6 carbon atoms such as trifluoroacetoxy group, or a substituted or unsubstituted aroyloxy group containing 7 to 11 carbon atoms such as benzoyloxy group or 2-methyl-6-nitrobenzoyloxy group. X is most preferably a halogen atom or 2-methyl-6-nitrobenzoyloxy group.

The compounds of formula (II) are novel compounds. Particularly preferred compounds of formula (II) are those wherein $R^1$ is methyl group; the group of the formula:

is dimethylamino group or diethylamino group; and A is nitrile group, methoxycarbonyl group, or ethoxycarbonyl group.

The compounds of formula (I) wherein X is an acyloxy group are novel compounds. The acyloxy group is preferably an alkanoyloxy group containing 2 to 6 carbon atoms, a halogenated alkanoyloxy group containing 2 to 6 carbon atoms, or a substituted or unsubstituted aroyloxy group containing 7 to 11 carbon atoms.

Next, reaction steps involved in the production of compound (VI) starting from the substituted benzoic acid is described in detail. Compound (VI) is an intermediate in the production of the quinolonecarboxylic acid antibacterial and contains a mother nucleus common to the quinolonecarboxylic acid antibacterial.

Substituted Benzoic Acid→Compound (I)

The substituted benzoyl halide compound of formula (I) (wherein X is a halogen) is produced by reacting a substituted benzoic acid with a halogenating agent such as thionyl chloride or oxalyl chloride preferably at a stoichiometric ratio (molar ratio) of about 1:1. Exemplary solvents which may be used include ether compounds such as tetrahydrofuran, diethyl ether, dioxane, and dimethoxyethane; aromatic compounds such as benzene, toluene, and xylene; chlorinated compounds such as methylene chloride and chloroform; ester compounds such as methyl acetate and ethyl acetate; and nitrile compounds such as acetonitrile. The reaction is conducted at a temperature in the range of 0 to 170° C., preferably from room temperature to 110° C. Usually, the reaction proceeds smoothly at a temperature in the vicinity of room temperature. The reaction time which depends on the solvent and the reaction temperature chosen is generally in the range of 1 to 15 hours.

The substituted benzoyl anhydride of formula (I) is produced by reacting a substituted benzoic acid with an acid anhydride such as acetic anhydride, trifluoroacetic anhydride, or benzoic anhydride, preferably with 2-methyl-6-nitrobenzoic anhydride, preferably at a stoichiometric ratio (molar ratio) of about 1:1. The solvent used may be any of the solvents used for producing substituted benzoyl halides, and is preferably chlorinated compounds such as methylene chloride and chloroform. The reaction temperature is in the range of −20° C. to 100° C., preferably 20° C. to 80° C. The reaction time which depends on the solvent and the reaction temperature chosen is generally in the range of 2 to 10 hours.

Compound (I)→Compound (II)

The compound of formula (II) is produced by reacting the compound of formula (I) with the compound of formula (III) preferably at a stoichiometric ratio (molar ratio) of about 1:1, and more specifically, by using 0.8 to 3.0 equivalents, preferably 1.0 to 1.5 equivalents of a base in relation to the acid halide or acid anhydride (I). Exemplary bases which may be used include tertiary amines such as pyridine, triethylamine, N-methylpiperidine, and N,N-dimethylaminopyridine, and use of triethylamine is preferred. Exemplary solvents which may be used include ether compounds such as tetrahydrofuran, diethyl ether, dioxane, and dimethoxyethane; aromatic compounds such as benzene, toluene, and xylene; chlorinated compounds such as methylene chloride and chloroform; ester compounds such as methyl acetate and ethyl acetate; and nitrile compounds such as acetonitrile. The reaction is accomplished at a temperature in the range of 0 to 170° C., preferably from room temperature to 110° C.

After completion of the reaction, the product is collected by filtering off the salts precipitated as a result of the reaction and concentrating the filtrate; or by adding the reaction mixture which has been optionally concentrated to water, removing the salts that are produced, and extracting the filtrate with a water-insoluble organic solvent. The target product can be obtained in a high purity by removing the solvent from the extract. However, when further purification is required, a pure product may be isolated by using column chromatography.

Compound (II)→Compound (IV)

Compound (IV) is produced by reacting compound (II) with fluorocyclopropylamine or its salt such as tosylate preferably in the presence of a base such as triethylamine preferably at a stoichiometric ratio (molar ratio) of about 1:1. The solvent which may be used in this reaction is not particularly restricted as long as it does not interfere with the reaction, and exemplary solvents include ether compounds such as diethyl ether, tetrahydrofuran, and dioxane; aliphatic compounds such as hexane and cyclohexane; aromatic compounds such as benzene, toluene, and xylene; chlorinated compounds such as methylene chloride, chloroform, and carbon tetrachloride; and ester compounds such as methyl acetate and ethyl acetate. The reaction temperature is in the range of −20 to 100° C., preferably 0 to 50° C. The reaction time varies depending on the reaction temperature, and is from several minutes to 10 hours, and usually 2 hours or less.

Compound (IV)→Compound (V)

Compound (V) is produced by treating compound (IV) with a base. The solvents which may be used in this reaction include ether compounds such as diethyl ether, tetrahydrofuran, and dioxane; and aprotic polar solvents such as N,N-dimethylformamide, dimethylsulfoxide, hexamethylphosphoric triamide, sulfolane, and N-methylpyrrolidone, and use of N,N-dimethylformamide is preferred. The base which may be used includes sodium hydride, butyllithium, sodium methoxide, potassium t-butoxide, metallic sodium, sodium carbonate, potassium carbonate, and potassium fluoride, and use of potassium carbonate is preferred. The base is used in an amount of 1 to 20 equivalents, preferably 1 to 5 equivalents in relation to compound (IV). The reaction temperature varies depending on the base used and is typically in the range of from room temperature to 300° C., preferably from room temperature to 100° C. The reaction time varies depending on the reaction temperature and is in the range of 1 to 48 hours, typically 6 to 24 hours.

Compound (V)→Compound (VI)

Compound (VI) may be produced by the hydrolysis of compound (V). In this reaction, the hydrolysis may be conducted under either acidic or alkaline conditions as long as the quinolone skeleton is not decomposed. The acid used in the hydrolysis under acidic conditions includes inorganic acids such as hydrochloric acid, sulfuric acid and nitric acid, and carboxylic acids such as formic acid and acetic acid, and the reaction may be conducted at a temperature in the range of room temperature to 300° C., preferably room temperature to 100° C. The acid is preferably used in an amount of 1 to 50 equivalents, preferably 1 to 10 equivalents in relation to compound (VI). The reaction time may vary depending on the reaction temperature, and is typically in the range of 1 to 48 hours, usually 1 to 24 hours. The base used in the hydrolysis under alkaline conditions includes inorganic bases such as sodium hydroxide and potassium hydroxide, and the reaction may be conducted at a temperature in the range of from room temperature to 300° C., preferably from room temperature to 100° C. The base is used in an amount of 1 to 50 equivalents, preferably 1 to 10 equivalents in relation to compound (VI). The reaction time may vary depending on the reaction temperature, and is typically in the range of 1 to 48 hours, usually 1 to 24 hours.

The thus obtained compound (VI) may be reacted with a 3-(R)-(1-aminocyclopropyl)pyrrolidine having its amino group protected, and then, the protective group of the amino group may be removed to produce the quinolone carboxylic acid derivative represented by formula (A) which is useful as an antibacterial agent (see the following reaction scheme). Exemplary groups which may be used for protecting the amino group include alkoxycarbonyl groups, aralkyloxycarbonyl groups, acyl groups, aralkyl groups, alkyl groups, and substituted silyl groups. The reaction may be conducted under the conditions specified in WO02/40478. For example, the reaction may be conducted in the presence of a base such as triethylamine, and the reaction product may be hydrolyzed by using hydrochloric acid or the like to thereby detach the protective group. Compound (A) may also be isolated in the form of an acid addition salt or a hydrate thereof.

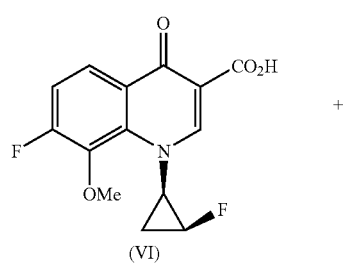

(VI)

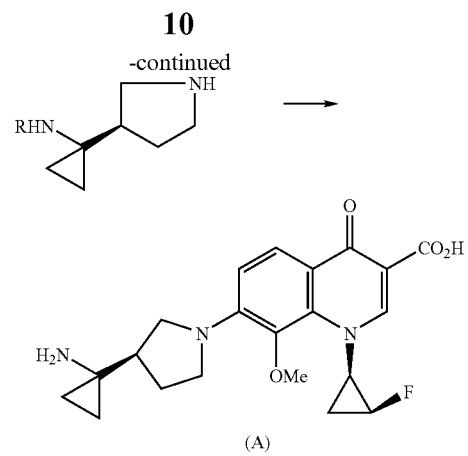

(A)

EXAMPLES

Next, the present invention is described in further detail by referring to the Examples and Reference Examples.

Example 1

Production of Ethyl 3-dimethylamino-2-(2,4-difluoro-3-methoxybenzoyl)acrylate

To 10.0 g of 2,4-difluoro-3-methoxybenzoic acid was added 40 mL of tetrahydrofuran. To this solution was added 0.4 mL of N,N-dimethylformamide, and then 8 mL of thionyl chloride was added dropwise with stirring to this mixture at room temperature. After completion of the dropwise addition, Dimroth condenser was installed, and the mixture was heated under reflux for 2 hours. After allowing the reaction mixture to cool, the solvent was distilled away. The resulting acid chloride was dissolved in 40 mL of tetrahydrofuran, and 12 ml of triethylamine was added to this solution and the mixture was stirred. After 30 minutes, 8.37 g of ethyl N,N-dimethylaminoacrylate was added dropwise, and after completing the dropwise addition, the mixture was heated under reflux for 2 hours. After completion of the reaction, the precipitated solid was removed by suction filtration, and the filtrate was concentrated under reduced pressure to obtain 23.3 g of the desired title compound as a dark brown oily compound.

$^1$H-NMR (400 MHz, CDCl$_3$) 0.94 (t, J=6.8 Hz, 3H), 3.97 (s, 3H), 3.98 (q, J=6.8 Hz, 2H), 6.91 (t, J=8.8, Hz, 1H), 7.20-7.30 (m, 1H), 7.77 (s, 1H).

Example 2

Production of Ethyl (E,Z)-2-(2,4-difluoro-3-methoxybenzoyl)-3-[(1R,2S)-fluorocyclopropylamine] acrylate To 22.3 g of ethyl 3-dimethylamino-2-(2,4-difluoro-3-methoxybenzoyl)acrylate was added 110 mL of ethyl acetate. While stirring the mixture at room temperature, 20.4 g of (1R,2S)-2-fluorocyclopropylamine tosylate was added, and then 1.5 g of triethylamine was added dropwise to the mixture. After 2 hours, 30 mL of water was added to the reaction mixture, and the mixture was extracted with 25 mL of ethyl acetate and dried with anhydrous sodium sulfate. Sodium sulfate was removed by filtration, and the filtrate was concentrated under reduced pressure to obtain 20.5 g of the title compound as a dark brown oily product.

Example 3

Production of Ethyl 7-fluoro-1-[(1R,2S)-2-fluorocyclopropylamine]-1,4-dihydro-8-methoxy-4-oxoquinoline-3-carboxylic acid To 20.5 g of ethyl (E,Z)-2-(2,4-difluoro-3-methoxybenzoyl)-3-[(1R,2S)-fluoro-cyclopropylamine]acrylate was added 40 mL of N,N-dimethylformamide, and the mixture was dissolved at room temperature. To the solution was added 12.5 g of potassium carbonate in powder form, and after the addition, the mixture was stirred at room temperature for 16.5 hours. After completion of the reaction, the reaction mixture was cooled in an ice bath, and 200 mL of water was gradually added dropwise. After completion of the dropwise addition, the precipitated crystals were filtered with suction. The resulting crude crystals were washed as a slurry with 40 mL of water, filtered, and further washed as a slurry with 120 mL of isopropyl ether. The resulting yellowish brown crystals were transferred to a dish, and air-dried to obtain 12.5 g of the title compound.

$^1$H-NMR (270 MHz, CDCl$_3$) 1.41 (t, J=7.3 Hz, 3H), 1.52-1.65 (m, 2H), 3.78-3.92 (m, 1H), 4.04 (d, J=2.0 Hz, 3H), 4.39 (q, J=7.3 Hz, 2H), 4.86 (ddt, J=62.4, 3.5, 5.4 Hz, 1H), 7.21 (dd, J=9.1, 10.4 Hz, 1H), 8.24 (dd, J=5.9, 9.1 Hz, 1H), 8.57 (d, J=1.4 Hz, 1H).

Example 4

Production of 7-fluoro-1-[(1R,2S)-2-fluorocyclopropylamine]-1,4-dihydro-8-methoxy-4-oxoquinoline-3-carboxylic acid 2N aqueous solution of sodium hydroxide (180 mL) was added dropwise to 32.4 g of the ethyl 7-fluoro-1-[(1R,2S)-2-fluorocyclopropylamine]-1,4-dihydro-8-methoxy-4-oxoquinoline-3-carboxylate at room temperature, and the mixture was stirred at 50° C. for 0.5 hour. After confirming disappearance of the starting materials, the reaction mixture was allowed to cool, 160 mL toluene was added dropwise thereto, and the mixture was stirred for 10 minutes. The solution was separated and an aqueous layer was added dropwise to 180 mL of 3N hydrochloric acid cooled in an ice bath. The precipitated crystals were filtered with suction, 160 mL of water was added thereto, and the resulting slurry was stirred at room temperature. After 15 minutes, the slurry was filtered again to obtain yellow crude crystals. To the thus obtained crude crystals was added 320 mL of acetonitrile, and the mixture was heated under reflux to completely dissolve the crystals. The solution was cooled with stirring to an internal temperature of 0° C. to precipitate crystals. The crystals were separated by filtration to obtain the title compound as whitish-yellow crystals (22.14 g).

$^1$H-NMR (270 MHz, CDCl$_3$) 1.55-1.73 (m, 2H), 4.01 (m, 1H), 4.10 (d, J=2.0 Hz, 3H), 4.80-4.84 (md, J=62.7 Hz, 1H), 4.96-5.00 (md, J=62.7 Hz, 1H), 7.35 (dd, J=9.0, 10.3 Hz, 1H), 8.27 (dd, J=5.9, 9.0 Hz, 1H), 8.85 (s, 1H), 14.52 (br s, 1H).

Analysis of the pale white crystals

Calculated value for C$_{14}$H$_{11}$F$_2$NO$_4$: C, 56.95; H, 3.76; N, 4.74; F, 12.87.

Measured value: C, 56.80; H, 3.73; N, 4.76; F, 12.83.

Example 5

Production of Ethyl 3-dimethylamino-2-(2,4-difluoro-3-methoxybenzoyl)acrylate (Mixed Acid Anhydride Method)

To 376 mg of the 2,4-difluoro-3-methoxybenzoic acid was added 40 mL of tetrahydrofuran. After adding 0.75 ml of triethylamine, 20 mg of N,N-dimethylaminopyridine and 689 mg of 2-methyl-6-nitrobenzoic anhydride to this solution, the mixture was stirred at room temperature. After 2 hours, mixed acid anhydrides were confirmed by TLC, and 430 mg of ethyl N,N-dimethylaminoacrylate was added dropwise thereto. After completion of the dropwise addition, the mixture was stirred for 24 hours. After completion of the reaction, water was added to the reaction mixture, and the separated solution was extracted with ethyl acetate and dried with anhydrous sodium sulfate. After removing the sodium sulfate by filtration, the filtrate was concentration under reduced pressure to obtain 511 mg of a dark brown oily product. The resulting residue was purified by silica gel column chromatography to obtain the title compound.

The invention claimed is:

1. A method for producing a compound represented by the following formula (VI):

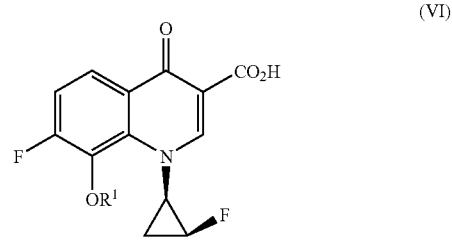

(VI)

wherein R$^1$ represents a lower alkyl group which comprises the steps of treating a compound represented by formula (IV):

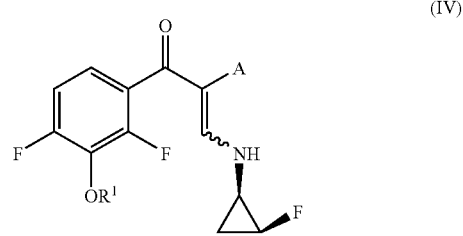

(IV)

wherein R$^1$ is as defined above and A represents nitrile group or an alkoxycarbonyl group with potassium carbonate in DMF to produce a compound represented by formula (V):

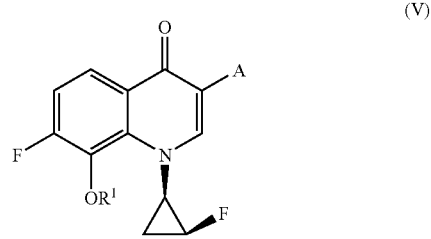

(V)

wherein R$^1$ and A are as defined above, and hydrolyzing this compound.

2. The method according to claim 1, wherein the compound represented by formula (IV) is produced by reacting a compound represented by formula (II):

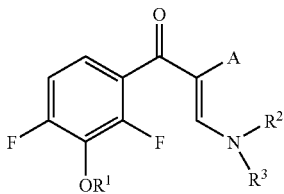

wherein $R^2$ and $R^3$ are the same or different lower alkyl groups and $R^1$ and A are as defined above with (1R,2S)-2-fluorocyclopropylamine.

3. The method according to claim 2, wherein the compound represented by formula (II) is produced by reacting a compound represented by formula (I):

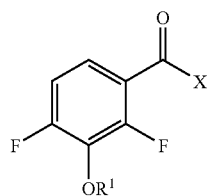

wherein $R^1$ is a lower alkyl group and X represents a halogen atom or an acyloxy group with a compound represented by formula (III):

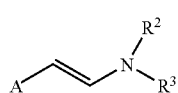

wherein A, $R^2$ and $R^3$ are as defined above.

4. The method according to claim 3, wherein the compound represented by formula (I) is produced by reacting a compound represented by formula:

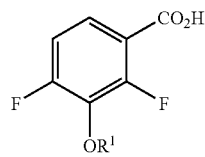

wherein $R^1$ and X are as defined above with a halogenating agent or an acid anhydride.

5. The method according to claim 1, wherein the group A is a nitrile group.

6. The method according to claim 2, wherein $R^2$ and $R^3$ are methyl groups.

7. The method according to claim 1, wherein $R^1$ is a methyl group.

8. The method according to claim 3, wherein X is a halogen atom or 2-methyl-6-nitrobenzoyl oxy group.

9. The method according to claim 4, wherein the compound of formula (I) is reacted with 2-methyl-6-nitrobenzoic anhydride.

10. The method according to claim 4, wherein the compound of formula (I) is reacted with at least one selected from the group consisting of acetic anhydride, trifluoroacetic anhydride and benzoic anhydride.

11. The method according to claim 4, wherein the compound of formula (I) is reacted with a halogenating agent or an acid anhydride at about a 1:1 stoichiometric ratio.

12. The method according to claim 2, wherein the compound of formula (II) is reacted with (1R,2S)-2-fluorocyclopropylamine in an acid form.

13. The method according to claim 1, wherein the hydrolyzing is carried out without decomposing the quinoline skeleton of the compound of formula (V).

14. The method according to claim 1, further comprising:
reacting the compound of formula (VI) with a compound of formula

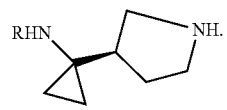

15. The method according to claim 1, wherein the compound represented by formula (IV) is treated with potassium carbonate in DMF at a temperature of from room temperature to 100° C. for a period of from 1 to 24 hours.

16. The method according to claim 1, wherein the compound of formula (IV) is treated with five equivalents of potassium carbonates in relation to the compound of formula (IV).

* * * * *